United States Patent [19]

Andrejasich et al.

[11] Patent Number: 4,646,069
[45] Date of Patent: Feb. 24, 1987

[54] FLUID DETECTION SYSTEM

[75] Inventors: Raymond J. Andrejasich, Carmel; Roy E. Kidd, Clayton, both of Ind.

[73] Assignee: Emhart Industries, Inc., Indianapolis, Ind.

[21] Appl. No.: 747,714

[22] Filed: Jun. 24, 1985

[51] Int. Cl.$^4$ ............................................. G01B 21/00
[52] U.S. Cl. .................................. 340/603; 340/605; 340/620; 73/40.5 R; 73/61.1 R
[58] Field of Search ................... 73/40.5 R, 49.1, 40, 73/61; 340/603, 605, 620

[56] References Cited

U.S. PATENT DOCUMENTS

| | | | |
|---|---|---|---|
| 3,882,465 | 5/1985 | Cook et al. | 340/825.07 |
| 3,935,567 | 1/1976 | Reynolds | 340/605 |
| 3,978,468 | 8/1976 | Bond et al. | 340/603 |
| 4,043,180 | 8/1977 | Morris et al. | 340/605 |
| 4,088,985 | 5/1978 | Saito et al. | 340/605 |
| 4,088,987 | 5/1978 | Resler et al. | 340/605 |
| 4,090,193 | 5/1978 | Hinkle, Jr. | 340/605 |
| 4,116,045 | 9/1978 | Potter | 73/61.1 R |
| 4,221,125 | 9/1980 | Oliver et al. | 73/61.1 R |
| 4,357,113 | 11/1982 | Brooks | 340/605 |
| 4,451,894 | 5/1984 | Dougherty et al. | 340/620 |

FOREIGN PATENT DOCUMENTS 95242 6/1983 Japan ........................................ 73/40

OTHER PUBLICATIONS

Pollulert TM Brochure #P-103, p. 3, (Mallory Component Group, Indianapolis).

Primary Examiner—Michael J. Tokar
Assistant Examiner—Hezron E. Williams
Attorney, Agent, or Firm—Robert F. Meyer; Carl A. Forest

[57] ABSTRACT

A fluid detection system capable of displaying the conditions in the environs of a large number of fluid detection probes and correlating each condition with the particular probe that detected it. There are a plurality of probes, each having a comparator preset with a unique probe identifier, such as a binary number. A counter produces digital signals representative of the binary numbers. The probe comparators are responsive to the numbers outputted by the counter and are connected to the probe power circuitry. When each comparator receives the signal corresponding to its preset number, it triggers its associated probe to produce status signals. A display circuit responds to both the number output by the counter and the probe status signals to simultaneously display the probe number and an indication of probe status.

1 Claim, 3 Drawing Figures

FLUID DETECTION SYSTEM

BACKGROUND OF THE INVENTION

1. Field of the Invention

The invention in general relates to fluid detection systems, such as for detecting the presence of fluid pollutants, and in particular a detection system having a large number of probes that can be individually identified and monitored from a central location

2. Description of the Prior Art

U.S. Pat. No. 4,221,125, on an invention of John N. Oliver and Louis M. Sandler and No. 4,116,045 on an invention of Bronson M. Potter are exemplary of systems for detecting the presence of fluid pollutants. Such systems typically involve detection probes that are buried or otherwise placed in the region of possible sources of pollutants, such as gasoline storage tanks. The probes are connected via wires to a central station which monitors the probe status. It is well known in the field that it is important to place a multiplicity of probes about such possible pollution sources so that leakage from any portion of the source and flowing in any direction will be quickly detected.

In one type of prior art fluid detection system, each probe is connected via its own set of wires to a centrally located multiplexer which, in combination with a microprocessor, individually interrogates each of the probes and determines its status, such as whether it is in contract with air, oil, or water. The front panel of the central unit has a set of lights for each probe; e.g. if there are four probes, there will be four sets of lights. The microprocessor actuates the lights associated with each probe to indicate the status of the probe. This system is relatively expensive due to the redundancy of electronic parts and the fact that the probes typically are at large distances (up to 4000 ft) from the central unit and separate connecting wiring is necessary for each probe. In addition, the microprocessor and associated display is relatively expensive. Other systems eliminate the expensive redundancy by utilizing parallel connections to the probes and a single display which is activated if any of the probes detect a pollutant or other sensed condition of interest. However, when a pollutant is detected by such a parallel system, an attendant must then go to each probe and check its status to determine which of the probes detected the condition of interest. Since probes are often long distances apart, this is very time consuming.

SUMMARY OF THE INVENTION

The fluid detection system of the invention automatically correlates the detected status of each probe with the particular probe, but is much less expensive than the prior art systems which correlated the probe status with particular probes.

The invention provides a fluid detection system in which relatively inexpensive parallel probe wiring may be used and which at the same time provides an output which uniquely identifies each probe while indicating the status of the probe.

The invention comprises a plurality of probe means for detecting the fluid state of their environment, means for producing a plurality of probe signals, one signal uniquely associated with each of the probes, a plurality of comparator means for comparing the probe signals to a predetermined probe identifier and for producing a status signal indicative of the environment of the probe upon reception of the probe signal corresponding to the identifier, one of the comparator means being associated with each of the probes, and an output means responsive to the probe signals and the status signals for producing an indication of the detected fluid state correlated with each of the probes.

Preferably, the probe signal is a digital signal corresponding to a binary number. In the preferred embodiment of the invention, the means for producing the probe signals includes a counter and a means for resetting the counter when it has counted up to a number equal to the number of probes. Preferably, there is a switch for setting the number at which the resetting means resets the counter so that the system may be adjusted to different numbers of probes. Preferably the comparator means includes a switch for setting the identifier. In the preferred embodiment, the output means comprises a means for displaying a number identifying the probe and a means for displaying symbols indicative of the probe environment status. Preferably, the means for displaying status symbols is a segmented electronic number display having at least three horizontal segments, and the different states, such as air, oil or water, are indicated by activating different ones of the horizontal segments.

Numerous other features, objects and advantages of the invention will become apparent from the following detailed description when read in conjunction with the accompanying drawings.

DESCRIPTION OF THE PREFERRED EMBODIMENT

Figure 1:
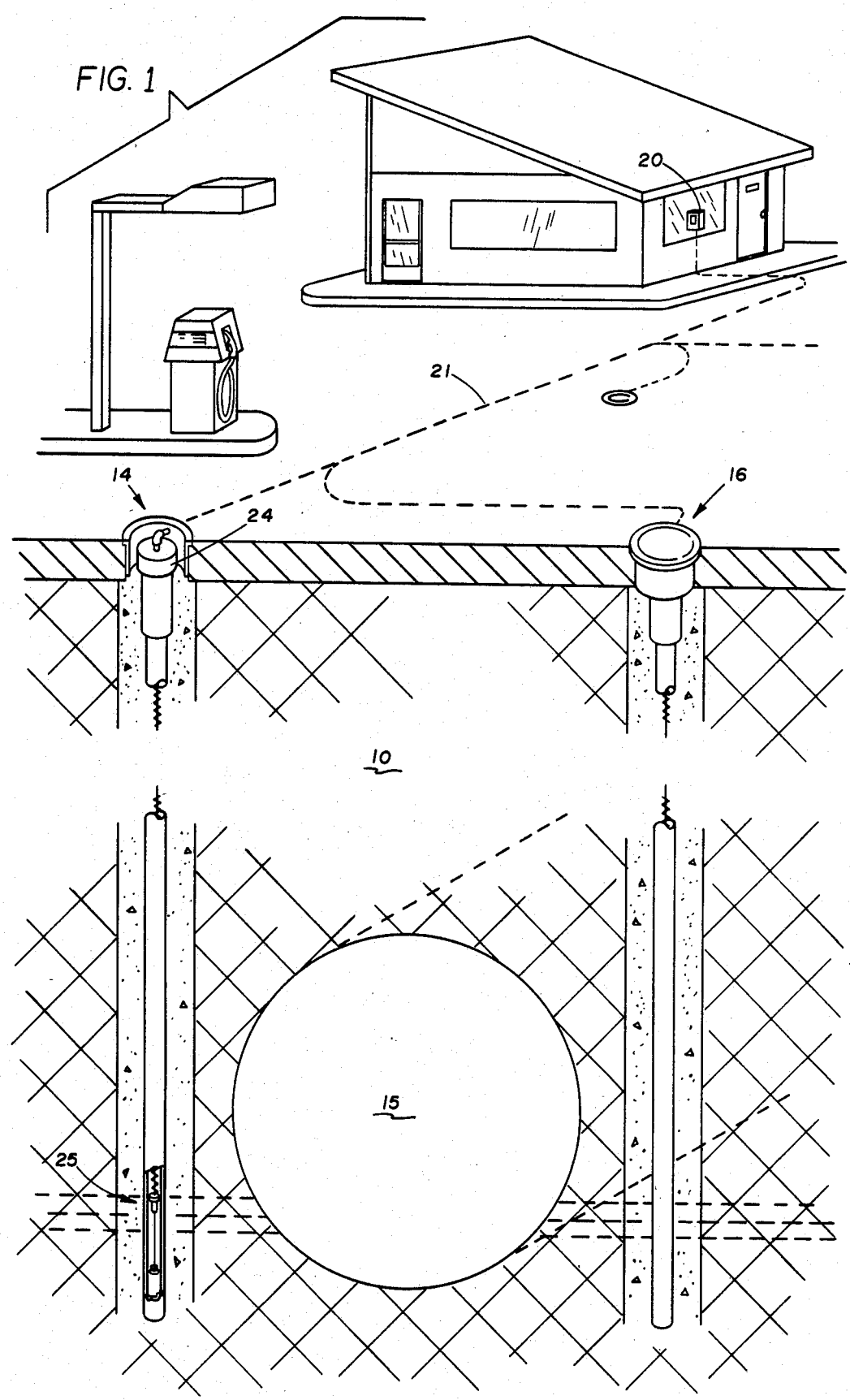
FIG. 1 is a diagramatic view of the invention in a typical operating environment.

Directing attention to FIG. 1, a diagramatic view of the invention as it may be installed at a service station, a typical operating environment, is shown. In the foreground 10 is a partial sectional view of the underground environment showing probe assemblies 14 and 16 on either side of a gasoline storage tank 15.

In the preferred embodiment of the invention, central interrogator circuit 20 provides a probe signal which is sent out along cable 21 to the probe assemblies 14, 16. An electronic assembly, such as 24, within each probe assembly contains a comparator (FIG. 3) which is preset with an identifier. Upon reception of the probe signal corresponding to the identifier, the comparator triggers a probe status circuit which checks the status of probe 25 and produces a probe status signal which passes back along cable 21 to central unit 20 which displays the status and identifies the probe.

Figure 2:
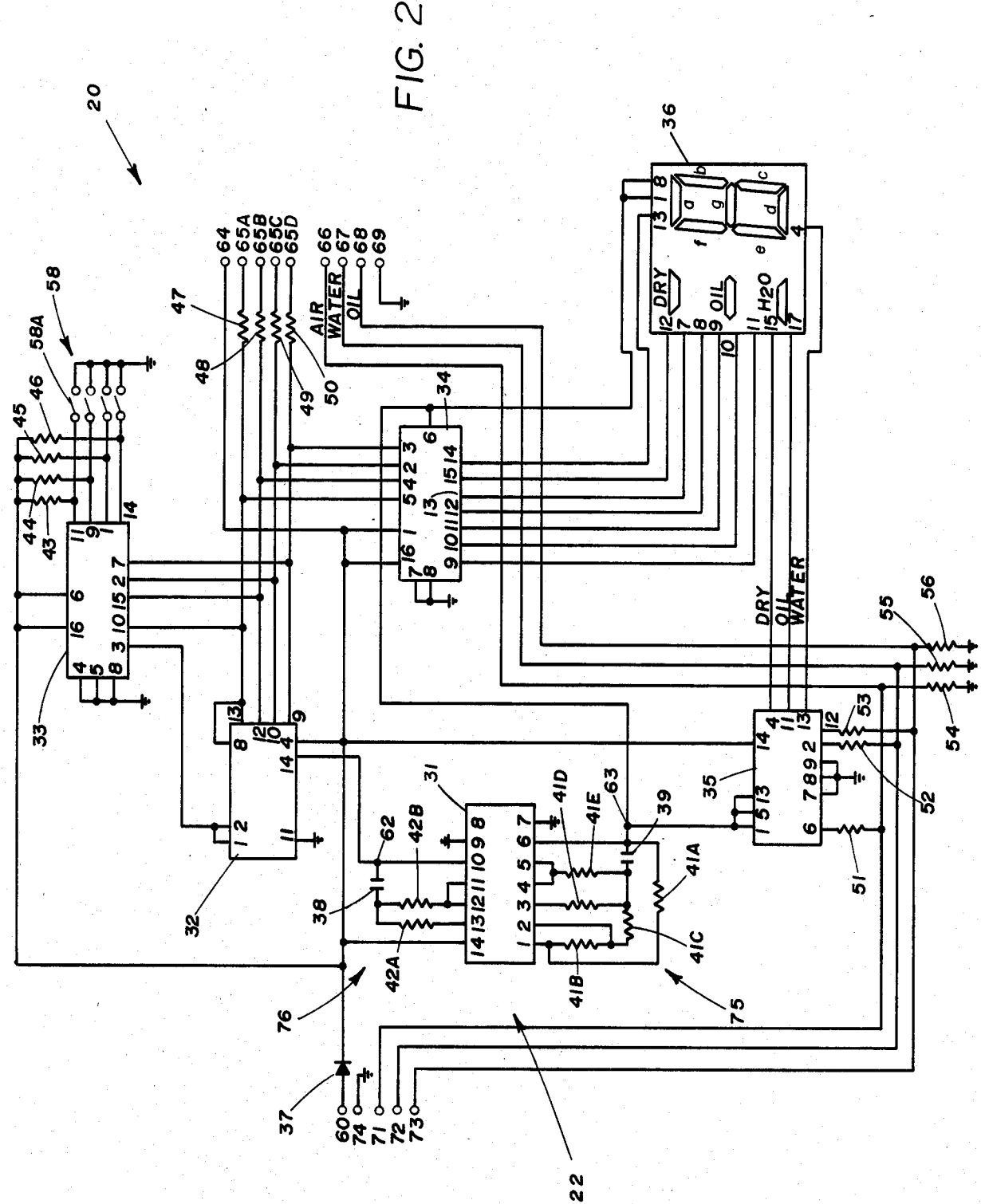
FIG. 2 is a diagram of one portion of the electronic circuitry of the preferred embodiment of the invention.

For a more detailed description of the invention, we turn now to FIG. 2 which shows the preferred electronic circuitry for the central probe interrogator unit 20. The circuitry of this embodiment includes integrated circuit chips 31, 32, 33, 34 and 35, two-digit liquid crystal display 36, diode 37, capacitors 38 and 39, resistors 41 through 56, and quadruple switch 58. The means 22 for producing a plurality of probe signals includes IC's 31, 32 and 33, while the output means 24 includes IC's 34 and 35 and display 36.

Power for the circuitry is provided via input 60 which may be connected to the power output of one of the prior art central monitor stations. The circuit shown is designed to operate at between 8 and 15 volts which we shall designate V+ herein. Diode 37 is preferably a type IN4001. Input 60 is connected to the anode of diode 37 and the cathode of the diode is connected to the various parts of the circuit which require the V+ supply, as will be indicated below.

Integrated circuit 31 is preferably a type CD4069 inverter which in the preferred embodiment is connected as follows: The No. 14 pin is connected to the V+ power supply, and the Nos. 7 and 9 pins are grounded; 47K ohm resistor 41A is connected across pins No. 1 and 6, 22K ohm resistor 41B is connected across pins 1 and 2, and pin 2 is connected to pin 6 through 39K ohm resistor 41C and 1.0 microfarad capacitor 39; Pin 3 is tied to the line between capacitor 39 and resistor 41C through 100K ohm resistor 41D while pins 4 and 5 are connected to the same line through 10K ohm resistor 41E; Pin Nos. 13 and 10 are connected through 100K ohm resistor 42A and 1.0 microfarad capacitor 38; Pins 11 and 12 are connected to the line between resistor 42A and capacitor 38 through 3.3 megohm resistor 42B. In this arrangement, the inverter 31 and the circuit below it form an oscillator circuit 75 with a frequency of 60 Hz, and the inverter 31 and the circuit above it form an oscillator circuit 76 with a period of approximately six seconds. The 60 Hz signal of oscillator 75 is output at point 63, while the six second period signal of oscillator 76 is output at point 62.

Integrated circuit 32 is preferably a 4-bit binary counter such as a MM74C93N. The output signal of oscillator 76 is input to the No. 14 pin of counter 32. The positive input voltage, V+, is applied to the No. 4 pin. The No. 1 and 2 pins (the reset inputs) are connected, as are the No. 8 and 13 pins. The No. 11 pin is grounded. The No. 9, 10, 12, 13 and 8 pins are outputs which are applied to the probe interface (FIG. 3) through protective 15K ohm resistors 47, 48, 49 and 50.

Integrated circuit 33 is preferably a 4-bit magnitude comparator. V+ is applied to the No. 6 and 16 pins of the comparator. The No. 4, 5, and 8 pins are grounded. The No. 10, 15, 2 and 7 input pins are connected to the No. 13, 12, 10 and 9 output pins, respectively, of counter 32. The number 11, 9, 1 and 14 pins of comparator 33 are connected to one side of the four switches, respectively, of quad switch 58. The other side of each of switches 58 is connected to ground. The No. 11, 9, 1, and 14 pins of comparator 33 are also connected to V+ through 100K ohm resistors 43 through 46. The No. 3 output pin is connected to the reset pins 1 and 2 of counter 32.

Integrated circuit 34 is preferably a BCD-to-7 segment decoder/driver for liquid crystal display 36. In the embodiment shown, driver 34 is a type CD4543. V+ is applied to the No. 1 and 16 pins of driver 34 and the No. 7 and 8 pins are grounded. The No. 6 pin is connected to the 60 Hz output line at 63. The No. 3, 2, 4 and 5 pins of decoder/driver 34 are connected to the 9, 10, 12 and 13 outputs, respectively, of counter 32.

Liquid crystal display 36 is preferably a Hamlin 3935-365-020. The Nos. 1 and 18 pins of display 36 are connected to the 60 Hz output at 63. The No. 11, 10, 9, 8, 7, 12 and 13 pins are connected to the No. 9, 10, 11, 12, 13, 15 and 14 output pins respectively of decoder/driver 34.

Integrated circuit 35 is preferably a QUAD-EXCLUSIVE-OR gate type CD4030AB. The No. 14 pin of QUAD gate 35 is connected to the V+ input voltage. The No. 1, 5 and 13 pins are connected to the 60 Hz output at 63. The No. 7, 8, and 9 pins are grounded. The No. 6, 2, and 12 inputs of gate 35 are connected to the probe status lines 66, 67 and 68, respectively, through 15K ohm resistors 51, 52 and 53 respectively. The probe status lines 66, 67 and 68 are also connected to ground through 100K ohm "pull-down" resistors 54, 55 and 56 respectively and are connected to interrogator outputs 71, 72 and 73, respectively. The No. 4, 11 and 13 output pins of gate 35 are connected to the No. 15, 17 and 4 pins, respectively, of liquid crystal display 36. Inputs 74 and 69 are grounded to provide a common ground for the complete system.

Figure 3:
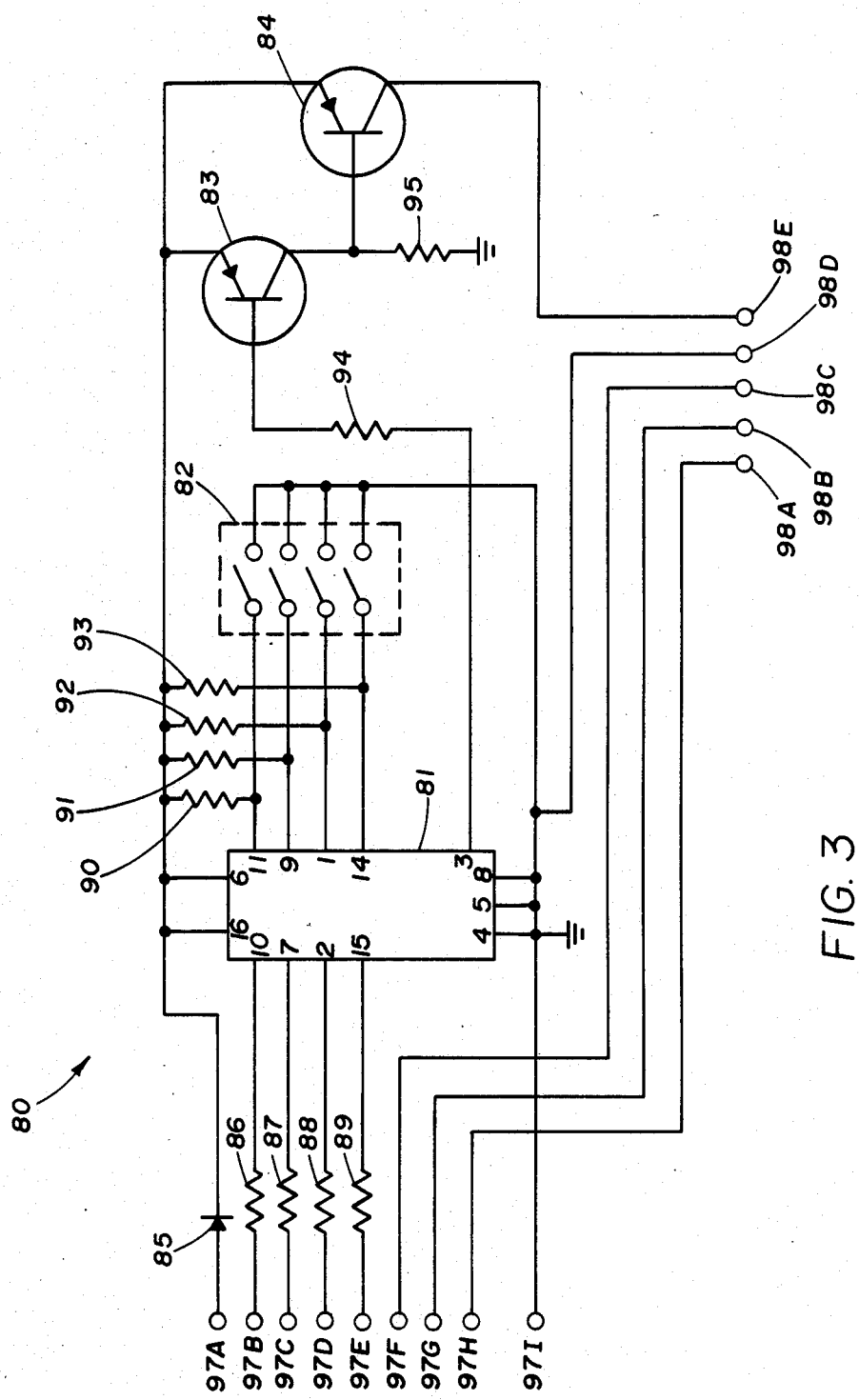
FIG. 3 is a diagram of the remaining portion of the electronic circuitry of the preferred embodiment of the invention.

Turning now to FIG. 3, the probe interface circuitry 80 is shown. This circuitry 80 provides a means 81 for comparing the probe signals outputted by the interrogator 20 to a predetermined probe identifier. Together with other circuitry in probe electronics module 24, circuitry 80 provides a means for producing a status signal indicative of the fluid environment of the probe. The interface circuitry 80 preferably includes integrated circuit 81, quad switch 82, pnp transistors 83 and 84, diode 85, resistors 86 through 95, and terminals 97A through 97I, and 98A through 98E. The V+ voltage from the interrogator unit 20 terminal 64 (FIG. 2) is applied to the input 97A which is connected to the anode of diode 85, which is preferably a type IN4001.

Integrated circuit 81 is preferably a 4-bit magnitude comparator such as type MM47C85N. The inputs 97B through 97E are connected to the outputs 65A through 65D, respectively, of the interrogator 20, and are also connected to the No. 10, 7, 2 and 15 pins, respectively, of comparator 81. The No. 4, 5 and 8 inputs of comparator 81 are connected to ground. The No. 11, 9, 1 and 14 pins are connected to one side of the switches of quad switch 82 and also to the cathode of diode 85 through 100K ohm resistors 90 through 93. The other side of the switches of quad switch 82 are connected to ground.

The No. 3 output pin of comparator 81 is applied to the base of transistor 83 through 10K ohm resistor 94. The emitter of transistor 83 is connected to the V+ voltage and the collector is applied to the base of transistor 84 and to ground through 10K ohm resistor 95. The emitter of transistor 84 is connected to the V+ voltage and the collector provides the power output to the probe, such as 25 (FIG. 1).

The remainder of the probe electronic unit 24 and the probe 25 itself may be a conventional probe with its associated electonics, for example, any of the probes FD221G, FD241G, FD241S or FD221T (which include the probe electronics) sold by Pollulert Systems, Mallory Componets Group, Indianapolis, Ind. 46206-07-Q6. The connections to the conventional probes are as follows: 98E connects to the probe power input, 98D to the probe ground and 98A, 98B, and 98C to the probe status outputs.

Turning now to the operation of the preferred embodiment of the invention, we refer back to FIG. 2. The user sets the switches in quad switch 58 to correspond to the number of probes. Normally the input pins 11, 9, 1, and 14 to comparator 33 are held high by the voltage applied to input 60. However, closing any one of the switches in quad switch 58 will ground the corresponding line and pin, with the corresponding one of resistors 43 through 46 preventing it from returning to V+ until after the switch is opened. Thus by setting switch 58 a combination of highs and lows corresponding to a binary number (high=1, low=0) from 0 to 9 will be placed on the comparator 33 input. For example, if switch 58A is open and the other three switches are closed, the binary number 0001=1 is input to comparator 33.

The oscillator 76 applies a trigger pulse to counter 32 every six seconds via line 62. The counter outputs a binary number from 0 to 9 on the lines connected to the outputs 65A through 65D, increasing the number one unit each time it is pulsed. The numbers put out by the counter 32 are a series of probe signals each of which is uniquely associated with one of the probes 25. The comparator 33 reads the number output by counter 32 and compares it with the number input from switch 58. When the numbers are the same, the comparator resets the counter 32 to zero, and the cycle repeats.

The binary output of counter 32 is sent via output terminals 65A through 65D (FIG. 2) to each of the probe assemblies 14. Each of the probe assemblies 14 includes a probe interface such as described in relation to FIG. 3. The comparator 81 in each probe assembly is set to a predetermined probe identifier, which in the case of this embodiment is a binary number set by quad switch 82 in a similar manner as just described above with respect to comparator 33 of FIG. 2. When comparator 81 receives the probe signal number corresponding to the preset identifier number, its output, pin 3, switches on the transistor pair 83 and 84 which applies the V+ voltage to its associated probe via output 98E. The probe outputs its status to terminals 98A, 98B, and 98C which signals are passed on to interrogator 20 (FIG. 2) via its probe terminals 66, 67 and 68.

The output of counter 32 is also applied to decoder/driver 34 which increments the right-hand digit of LCD display 36 each time counter 32 is pulsed by the six second oscillator 76. The output of the 60 Hz oscillator 75 swings between the high and low voltages and is applied to the backplane of the LCD display 36 and the phase pin (pin 6) of driver 34 to provide the proper AC drive to the LCD for extended display life. The probe status input on terminals 66, 67 and 68 is applied to QUAD gate 35 which enables the left-hand digit of the LCD display 36. When the inputs and outputs are arranged as shown, the horizontal or "a", "g" and "d" segments of the seven-segment display digit are activated by a high signal on status inputs 66, 68 and 67, respectively. The Pollulert ® probes mentioned above provide status signals corresponding to the "air", "oil" and "water" conditions. These status conditions may be imprinted on the case of interrogator 20 opposite the corresponding one of the "a", "g" and "d" segments so that the appropriate condition is directly indicated when the segment is enabled.

Summarizing, with each pulse of the six second oscillator 76, counter 32 increments one digit, say from 2 to 3. The counter outputs the binary number, for example 0011 or 3 to the driver 34 which places a numeral 3 on display 36. The binary number 3 is also output to each of the probe interfaces. The interface having a comparator 81 set with the identifier 0011 (3) will turn on its associated probe to produce its probe status signal. The probe status signal is outputted via inputs 98A, 98B, and 98C and gates 35 to display 36. The status of probe number 3 will then be indicated on the left of display 36 while the number "3" is displayed at the right. After six seconds the status of probe 4 will be displayed.

The diodes 37 and 85 prevent damage to the circuitry if a negative voltage is inadvertently applied to the inputs 60 or 97A, respectively. Resistors 47 through 50 protect the circuit from high currents if the terminals 65A through 65D are accidently shorted. They also provide a certain degree of protection against electrostatic discharge (ESD). Resistors 43 through 46 are "pull-up" resistors which keep the associated lines high until the switches in quad switch 58 are closed. Resistors 54 through 56 are "pull-down" resistors to keep the inputs to gates 35 low until a status signal is received. Resistors 51 through 53 protect against short circuits on the input lines to the gates 35, as well as ESD protection. Likewise resistors 86 through 89 and 94 are protective resistors, resistors 90 through 93 are "pull-up" resistors and resistor 95 is a "pull-down" resistor.

In the preferred embodiment, the probe status signals are also output to a conventional central monitor via outputs 71, 72 and 73. This monitor may be located adjacent to interrogator 20 or some distance from it. The alarms and other sophisticated circuitry and programming within the monitor will function normally as though they were connected directly to the probes.

There has been described a novel apparatus for detecting fluid conditions whereby a large number of probes can be individually identified and monitored from a central location. It is evident that those skilled in the art may now make numerous uses and modifications of the specific embodiment described, without departing from the invention concepts. For example, probe signals other than numbers may be used. The means for comparing at each probe site may be a device other than the electronic comparator disclosed. The output means may take on a variety of forms, and need not be visual. Fluid pollutants other than oil may be detected. Many other variations and uses may be described. The particular values and types of electronic circuit parts, such as ICs, capacitors, resistors, etc., may be replaced with other equivalent parts. Consequently, the invention is to be construed as embracing each and every novel feature and novel combination of features present in and/or possessed by the fluid detection system described.

What is claimed is:

1. An apparatus for detecting the presence of fluids comprising:
   a plurality of probes for detecting the fluid state of their environment;
   means for producing a plurality of digital probe signals, each signal corresponding to a binary number, one number uniquely associated with each of said probes;
   a plurality of comparator means for comparing said probe signals to a predetermined probe identifier and for producing a status signal indicative of the fluid environment of the probe upon reception of the probe signal corresponding to the identifier, one of said comparator means being associated with each of said probes; and
   output means responsive to the probe signals and the status signals for producing an indication of the detected fluid state correlated with each of said probes, said means including at least two segmented electronic number displays, at least one of said displays responsive to said probe signal for displaying said numbers corresponding to said probes and another of said displays having at least three horizontal segments and wherein the different probe status conditions are indicated by activating a different one of said horizontal segments.

* * * * *